(12) United States Patent
Kasumi (10) Patent No.: US 10,441,133 B2
(45) Date of Patent: Oct. 15, 2019

(54) WIRELESS ENDOSCOPE

(71) Applicant: OLYMPUS CORPORATION, Hachioji-shi, Tokyo (JP)

(72) Inventor: Makoto Kasumi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/598,744

(22) Filed: May 18, 2017

(65) Prior Publication Data

US 2017/0251904 A1    Sep. 7, 2017

Related U.S. Application Data

(63) Continuation of application No. PCT/JP2016/063362, filed on Apr. 28, 2016.

(30) Foreign Application Priority Data

Aug. 18, 2015 (JP) ................................ 2015-161136

(51) Int. Cl.
*A61B 1/00* (2006.01)
*G02B 23/24* (2006.01)
(Continued)

(52) U.S. Cl.
CPC ...... *A61B 1/00032* (2013.01); *A61B 1/00009* (2013.01); *A61B 1/00016* (2013.01);
(Continued)

(58) Field of Classification Search
CPC ............ A61B 1/00027; A61B 1/00032; A61B 1/00034; A61B 1/00036; A61B 1/00105
See application file for complete search history.

(56) References Cited

U.S. PATENT DOCUMENTS

2003/0018238 A1    1/2003  Obata et al.
2007/0096870 A1*   5/2007  Fisher ................. E05B 19/0005
                                                        340/5.53
(Continued)

FOREIGN PATENT DOCUMENTS

CN        101541228 A     9/2009
EP          2042077 A1    4/2009
(Continued)

OTHER PUBLICATIONS

Aug. 2, 2016 Search Report issued in International Patent Application No. PCT/JP2016/063362.
(Continued)

*Primary Examiner* — Alexandra L Newton
(74) *Attorney, Agent, or Firm* — Oliff PLC (57) ABSTRACT

A wireless endoscope includes: a detection portion configured to detect a connection state to an endoscope body of a battery; and a control portion configured to set a replacement time operation mode of using the power from a power storage component as the power needed for the endoscopic observation and performing the endoscopic observation with lower power compared to a normal time operation mode of performing an endoscopic observation with the power from the battery, when a detection result of a non-connection state of the battery is given from the detection portion, in which the control portion restores the normal time operation mode from the replacement time operation mode when a detection result of a reconnection state to the endoscope body of the battery is given from the detection portion.

5 Claims, 5 Drawing Sheets (51) Int. Cl.
*A61B 1/045* (2006.01)
*A61B 1/06* (2006.01)
*H04N 5/225* (2006.01)
*H04N 5/232* (2006.01)
*A61B 1/04* (2006.01)

(52) U.S. Cl.
CPC .......... *A61B 1/00036* (2013.01); *A61B 1/041* (2013.01); *A61B 1/045* (2013.01); *A61B 1/06* (2013.01); *G02B 23/24* (2013.01); *G02B 23/2484* (2013.01); *H04N 5/2256* (2013.01); *H04N 5/23241* (2013.01); *H04N 2005/2255* (2013.01)

(56) References Cited

U.S. PATENT DOCUMENTS

| | | |
|---|---|---|
| 2007/0280630 A1 | 12/2007 | Komoda |
| 2008/0139881 A1 | 6/2008 | Cover et al. |
| 2010/0271468 A1 | 10/2010 | Wang |
| 2013/0013942 A1 | 1/2013 | Koshimizu |
| 2013/0324794 A1* | 12/2013 | Cover ................ A61B 1/00016 600/103 |

FOREIGN PATENT DOCUMENTS

| | | |
|---|---|---|
| JP | 2003-24267 A | 1/2003 |
| JP | 2007-329519 A | 12/2007 |
| JP | 2009-77875 A | 4/2009 |
| JP | 2010-131290 A | 6/2010 |
| JP | 2012-118152 A | 6/2012 |
| JP | 2013-37673 A | 2/2013 |
| WO | 2010/143721 A1 | 12/2010 |

OTHER PUBLICATIONS

Xinkai Chen et al., "A Wireless Capsule Endoscope System With Low-Power Controlling and Processing ASIC". IEEE Transactions of Biomedical Circuits and Systems, vol. 3, No. 1, pp. 11-22, Feb. 2009.

Jun. 25, 2018 Search Report issued in European Patent Application No. 16836831.4.

Dec. 29, 2018 Office Action issued in Chinese Patent Application No. 201680004834.7.

* cited by examiner

WIRELESS ENDOSCOPE

CROSS REFERENCE TO RELATED APPLICATION

This application is a continuation application of PCT/JP2016/063362 filed on Apr. 28, 2016 and claims benefit of Japanese Application No. 2015-161136 filed in Japan on Aug. 18, 2015, the entire contents of which are incorporated herein by this reference.

BACKGROUND OF THE INVENTION

1. Field of the Invention

The present invention relates to a wireless endoscope drivable with a battery.

2. Description of the Related Art

Conventionally, with progress in semiconductor technology, various kinds of equipment such as cellular phones, smartphones and tablet PCs have been miniaturized, reduced in power consumption, and configured to be portable. Portable equipment is often loaded with a battery and configured to be continuously usable by charging the battery.

Also in a medical field, miniaturization of devices has been accelerated, and in an endoscope of relatively large power consumption for example, a wireless endoscope loaded with a charging type battery has been developed. The wireless endoscope is used in various fields such as the medical field and an industrial field. The wireless endoscope in the medical field is used in observation of organs inside a body cavity, curative treatment using a treatment instrument, endoscopic surgery or the like. Note that, the wireless endoscope is disclosed in Japanese Patent Application Laid-Open Publication No. 2009-77875, and the proposal discloses a technology of compatibly preventing battery exhaustion during observation and efficiently utilizing a battery capacity.

A picked-up image obtained by the wireless endoscope is transmitted to a processor that performs image processing. By the processor, a medical image is displayed on a monitor and recorded in a recording medium. The wireless endoscope incorporates a wireless communication portion for transmitting an endoscopic image obtained by an image pickup device to the processor and a light source device for illuminating an object or the like, is wirelessly configured, and is therefore excellent in portability and workability.

When the portability is considered, weight of a battery loaded on the wireless endoscope is limited, and a battery capacity is also limited. Therefore, just by one battery loaded on the wireless endoscope, the wireless endoscope is not always driven in an entire period of a procedure that uses the endoscope. Therefore, it is needed to consider replacement of the battery in a middle of a procedure.

SUMMARY OF THE INVENTION

A wireless endoscope according to one aspect of the present invention includes: an image pickup portion configured to pick up an image of an object; a power storage component configured to hold power; a detection portion configured to detect a connection state to an endoscope body incorporating the image pickup portion and the power storage component of a battery attachably and detachably attached to the endoscope body, the battery being configured to generate power needed for endoscopic observation; and a control portion configured to set a replacement time operation mode of using the power from the power storage component as the power needed for the endoscopic observation and performing the endoscopic observation with lower power compared to a normal time operation mode of performing the endoscopic observation with the power from the battery, when a detection result of a non-connection state of the battery is given from the detection portion, wherein the control portion restores the normal time operation mode from the replacement time operation mode when a detection result of a reconnection state to the endoscope body of the battery is given from the detection portion.

DETAILED DESCRIPTION OF THE PREFERRED EMBODIMENT(S)

Hereinafter, an embodiment of the present invention will be described in detail with reference to the drawings.

Figure 1:
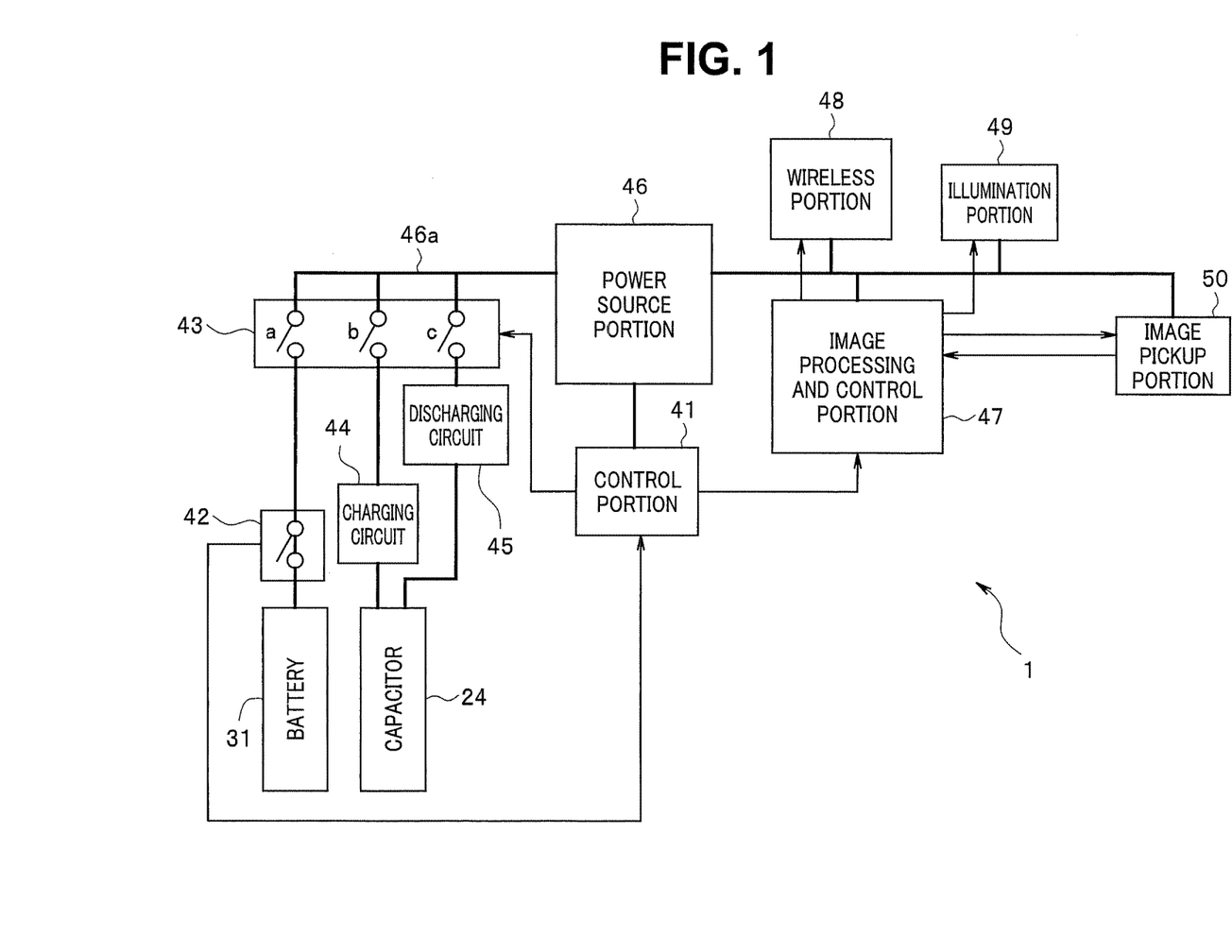
FIG. 1 is a block diagram illustrating a wireless endoscope relating to one embodiment of the present invention.
Figure 2:
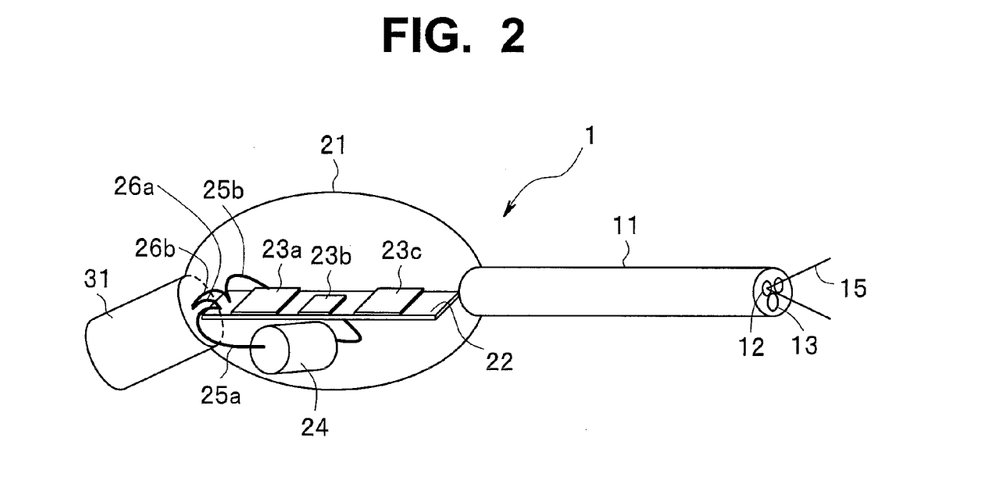
FIG. 2 is an explanatory diagram illustrating an appearance of the wireless endoscope in FIG. 1.
Figure 3:
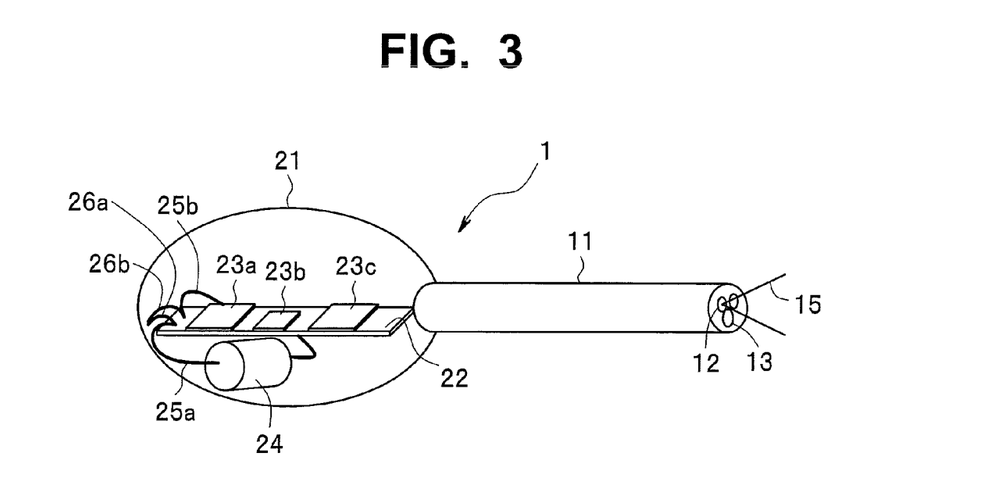
FIG. 3 is an explanatory diagram illustrating the appearance of the wireless endoscope in FIG. 1.

FIG. 1 is a block diagram illustrating a wireless endoscope relating to one embodiment of the present invention. In addition, FIG. 2 and FIG. 3 are explanatory diagrams illustrating an outline of the wireless endoscope in FIG. 1. Furthermore, FIG. 4 is an explanatory diagram illustrating an entire configuration of an endoscope system arranged in an operation room.

First, an outline of the endoscope system using the wireless endoscope will be described with reference to FIG. 2 to FIG. 4. FIG. 2 illustrates a state that a battery 31 is mounted on a wireless endoscope 1, and FIG. 3 illustrates a state that the battery 31 is detached from the wireless endoscope 1.

Figure 4:
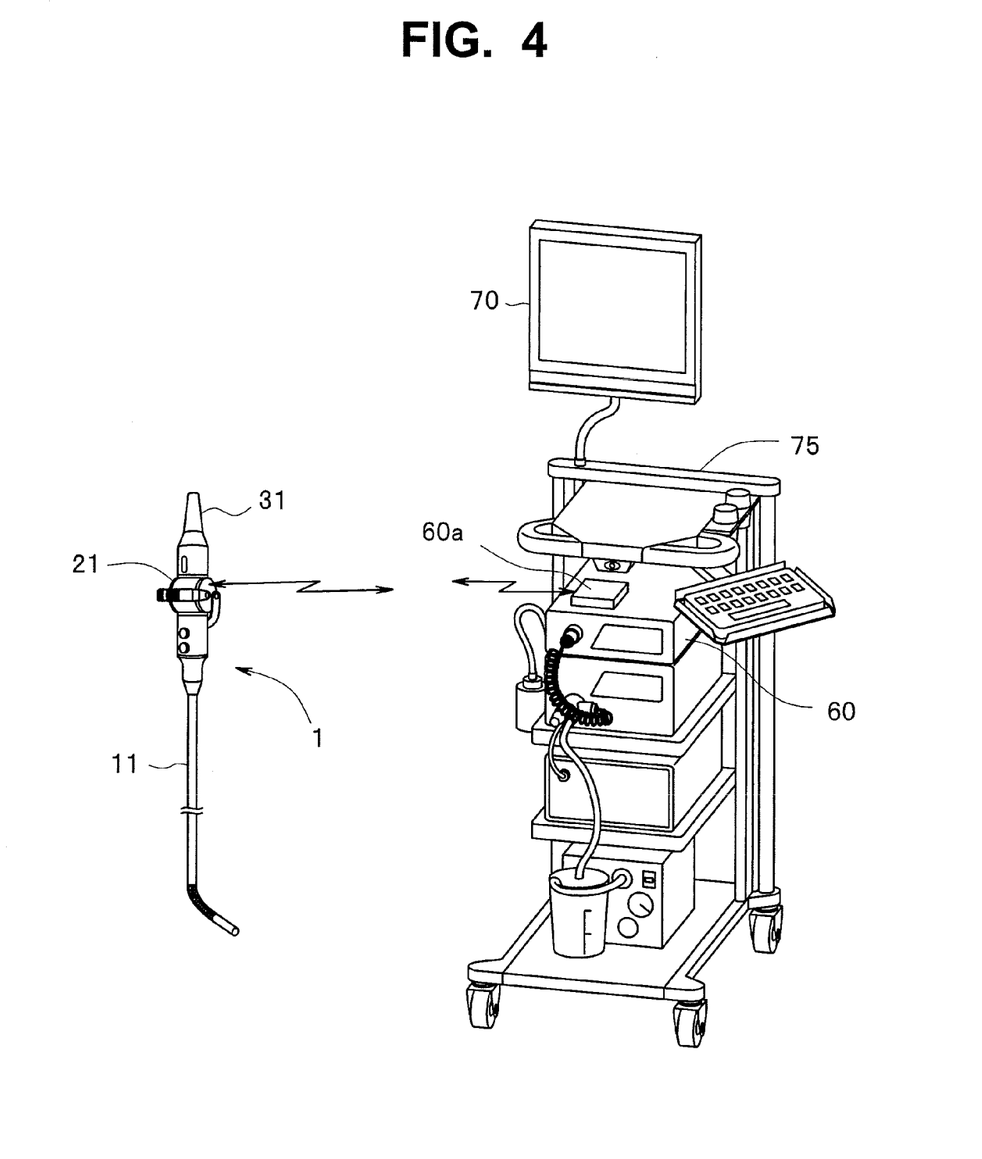
FIG. 4 is an explanatory diagram illustrating an entire configuration of an endoscope system arranged in an operation room.

As illustrated in FIG. 4, the endoscope system is configured by the wireless endoscope 1, a processor 60 and a monitor 70. As illustrated in FIG. 4, in the operation room, various kinds of medical equipment and the monitor 70 are arranged on a cart 75. On the cart 75, the processor 60 for which a wireless portion 60a is separately configured is mounted. The wireless portion 60a is connected to the processor 60 by a connector not illustrated in the figure. Note that, on the cart 75, as the medical equipment, devices such as an electrocautery device, a pneumoperitoneum device, and a video recorder, and a gas cylinder filled with carbon dioxide or the like are also mounted.

The wireless endoscope 1 can perform a photographing operation for normal endoscopic observation by mounting the battery 31, and is configured to be wirelessly connected with the processor 60.

The wireless endoscope 1 is configured by an endoscope body including an insertion portion 11 on a distal end side and including an operation portion 21 on a proximal end side. On a distal end portion of the insertion portion 11, an image pickup portion 50 (omitted in FIG. 2 to FIG. 4) including an image pickup device configured by a CCD, a CMOS sensor or the like is disposed. In addition, the insertion portion 11 is provided with an illumination portion 49 (omitted in FIG. 2 to FIG. 4) configured to generate illumination light for illuminating an object, and the light generated by the illumination portion 49 is radiated to the object as illumination light 15 through a lens 12 at a distal end of the insertion portion 11.

Return light from the object is made incident through a lens 13 at the distal end of the insertion portion 11, and an image is formed on an image pickup surface of the image pickup portion 50. The image pickup portion 50 obtains a picked-up image based on an object optical image by photoelectric conversion. The image pickup portion 50 transmits the picked-up image to a substrate 22 inside the operation portion 21 through a signal line not illustrated in the figure inside the insertion portion 11. On the substrate 22 provided in the operation portion 21, various kinds of ICs 23a to 23c are loaded. By the ICs 23a to 23c or the like, respective circuit portions in FIG. 1 are configured.

Note that, while the image pickup portion 50 and the illumination portion 49 are described as the portions provided on the distal end of the insertion portion 11, an image pickup portion may be provided on a side of the operation portion 21 like a camera head, and a light source may be provided on an operation portion side or the like and the illumination light may be guided to the distal end of the insertion portion 11 by a light guide or the like.

The operation portion 21 is provided with a battery connection portion not illustrated in the figure for mounting the battery 31, and the battery 31 can be attachably and detachably mounted on the battery connection portion. Power source lines 26a and 26b are connected to the battery connection portion, and the power source lines 26a and 26b can supply power from the battery 31 to a power source portion 46 loaded on the substrate 22.

In the present embodiment, inside the operation portion 21, a capacitor 24 that is a power storage component configured to hold the power is provided. The capacitor 24 can generate power needed for the endoscopic observation in a replacement time operation mode to be described later. Power source lines 25a and 25b are connected to the capacitor 24, and the capacitor 24 is charged by the battery 31 through the power source lines 25a and 25b. In addition, the power source lines 25a and 25b can supply the power from the capacitor 24 to the power source portion 46 loaded on the substrate 22.

Note that, in the present embodiment, since the capacitor 24 chargeable by the battery 31 is adopted as a component configured to hold the power, the power needed for the endoscopic observation can be held without detaching the capacitor 24 from the operation portion 21. Note that, as the power storage component, it is sufficient to hold the power capable of driving the wireless endoscope 1 when replacing the battery 31, and not only a chargeable capacitor and a secondary battery but also a primary battery may be adopted.

In FIG. 1, the wireless endoscope 1 is provided with a control portion 41. The control portion 41 can be configured by a processor such as a CPU not illustrated in the figure, and may be able to control respective portions according to a program stored in a memory.

In FIG. 1, a power supply line is illustrated by a thick line. The power source portion 46 receives power supply through a power source line 46a, and generates the power needed for the endoscopic observation. For example, the power source portion 46 generates the power to be supplied to the control portion 41, an image processing and control portion 47, a wireless portion 48, the illumination portion 49 and the image pickup portion 50 of the wireless endoscope 1. The illumination portion 49 receives the power supply from the power source portion 46, is controlled by the image processing and control portion 47, and generates the light for illuminating the object. The image pickup portion 50 receives the power supply from the power source portion 46, is driven by the image processing and control portion 47, picks up the image of the object, and outputs the picked-up image to the image processing and control portion 47.

The image processing and control portion 47 receives the power supply from the power source portion 46, executes predetermined image processing on the picked-up image from the image pickup portion 50, and then outputs the picked-up image to the wireless portion 48. For example, the image processing and control portion 47 is capable of image compression processing as the image processing. The wireless portion 48 that is a communication portion receives the power supply from the power source portion 46, is driven by the image processing and control portion 47, and wirelessly transmits the picked-up image to the processor 60 or the like through the wireless portion 60a. In the present embodiment, the image processing and control portion 47 is controlled by the control portion 41, and controls the respective portions in two operation modes that are a normal time operation mode and the replacement time operation mode as described later.

The battery 31 is connected to the power source portion 46 through a switch portion 43 and the power source line 46a. Between the battery 31 and the switch portion 43, a detection portion 42 configured to detect whether or not the battery 31 is in a detachable state is provided. The detection portion 42 can be configured by a mechanical switch including a lock mechanism that fixes the battery 31 to the battery connection portion of the operation portion 21, for example. By turning off the mechanical switch, the detachment of the battery 31 becomes possible. A detection result of the detection portion 42, that is, a result of detecting whether or not the battery 31 is in the detachable state, is supplied to the control portion 41.

Note that, while the detection portion 42 is described as the portion configured to detect whether or not the battery 31 is in the detachable state, the detection portion 42 may detect electric connection of the battery 31 or may detect that the battery 31 is electrically detached from the battery connection portion. In following description, the detection portion 42 is described as the portion configured to detect whether or not the battery 31 is in the detachable state, however, even when the detection portion 42 is the portion configured to detect whether or not the battery 31 is in the state of being not electrically connected to the battery connection portion, the embodiment is similarly applicable.

The capacitor 24 is connected to the power source line 46a through a charging circuit 44 and the switch portion 43, and is connected to the power source portion 46 through a discharging circuit 45, the switch portion 43 and the power source line 46a. The switch portion 43 is configured by a switch a configured to control the connection of the battery 31 and the power source line 46a, a switch b configured to control the connection of the charging circuit 44 and the power source line 46a, and a switch c configured to control the connection of the discharging circuit 45 and the power source line 46a. The charging circuit 44 can charge the capacitor 24 when the power from the battery 31 is supplied through the power source line 46a and the switch portion 43. The discharging circuit 45 can supply the power supplied from the capacitor 24 to the power source portion 46 through the switch portion 43 and the power source line 46a. In the switch portion 43, the respective switches a to c are on/off controlled by the control portion 41.

When it is indicated that the battery 31 is not in the detachable state by the detection result from the detection portion 42, the control portion 41 sets the normal time operation mode, turns on the switches a and b of the switch portion 43, and turns off the switch c of the switch portion 43. In the normal time operation mode, the power from the battery 31 is supplied to the power source line 46a through the switch portion 43, and the power source portion 46 generates the power to be supplied to the respective portions using the power from the battery 31. In addition, in the normal time operation mode, the power supplied from the battery 31 to the power source line 46a through the switch a is also supplied to the charging circuit 44 through the switch b. The charging circuit 44 charges the capacitor 24 using the power that is supplied to the power source line 46a.

Next, it is assumed that it is indicated that the battery 31 is in the detachable state by the detection result from the detection portion 42. In this case, the control portion 41 sets the replacement time operation mode, turns off the switches a and b of the switch portion 43, and turns on the switch c of the switch portion 43. In the replacement time operation mode, the power from the capacitor 24 is supplied to the discharging circuit 45. The power generated by the discharging circuit 45 is supplied to the power source line 46a through the switch portion 43, and the power source portion 46 generates the power to be supplied to the respective portions using the power from the capacitor 24.

The control portion 41 controls the image processing and control portion 47, and makes different processing be executed in the normal time operation mode and the replacement time operation mode. For example, the image processing and control portion 47 controls drive of the respective portions such that power consumption in the replacement time operation mode becomes lower compared to the normal time operation mode. For example, the image processing and control portion 47 may control the image pickup portion 50 so as to make a photographing frame rate in the replacement time operation mode be lower than the photographing frame rate in the normal time operation mode. In addition, for example, the image processing and control portion 47 may perform compression processing on the picked-up image so that an image compression ratio in the replacement time operation mode becomes higher than the image compression ratio in the normal time operation mode. Furthermore, for example, the image processing and control portion 47 may control the illumination portion 49 so as to make an illumination light quantity in the replacement time operation mode be lower than the illumination light quantity in the normal time operation mode. Further, the image processing and control portion 47 may control the wireless portion 48 and adopt a data transmission method, time division transmission for example, that the power consumption is reduced compared to the normal time operation mode in the replacement time operation mode.

For example, the image processing and control portion 47 may surely make the illumination light quantity of the illumination portion 49 in the replacement time operation mode be lower than the illumination light quantity in the normal time operation mode, and may arbitrarily adjust the compression ratio of the image and the photographing frame rate of the image pickup portion 50.

Next, an operation of the embodiment configured in this way will be described with reference to FIG. 5 to FIG. 7.

Figure 5:
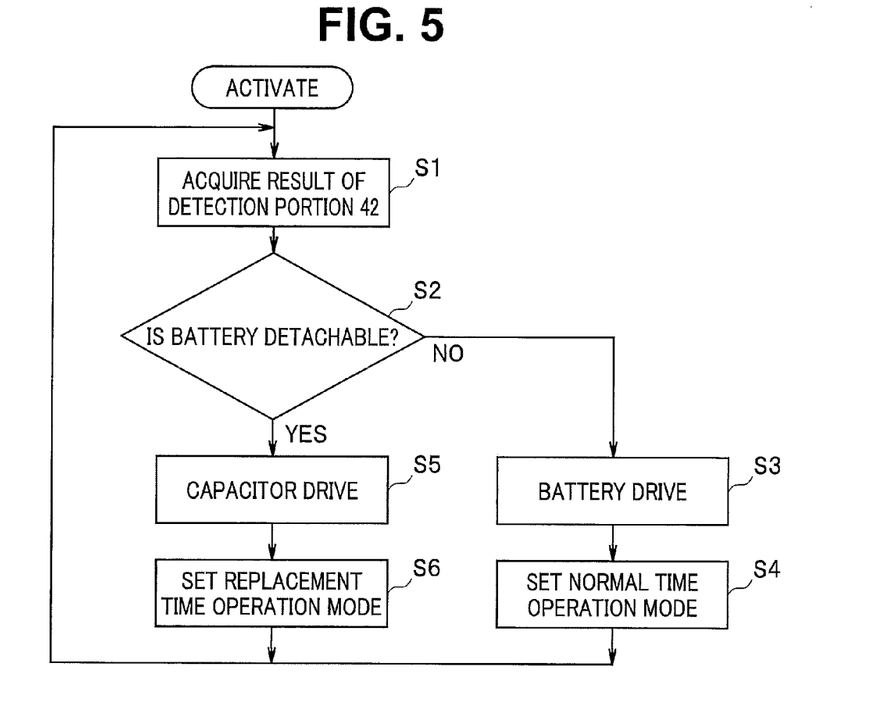
FIG. 5 is a flowchart for describing an operation of an embodiment.
Figure 6:
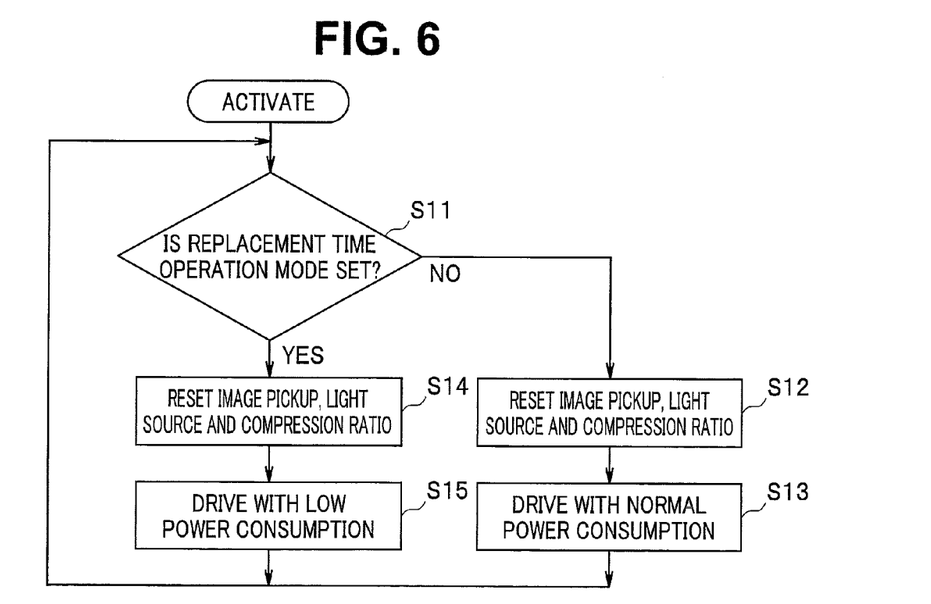
FIG. 6 is a flowchart for describing the operation of the embodiment.
Figure 7:
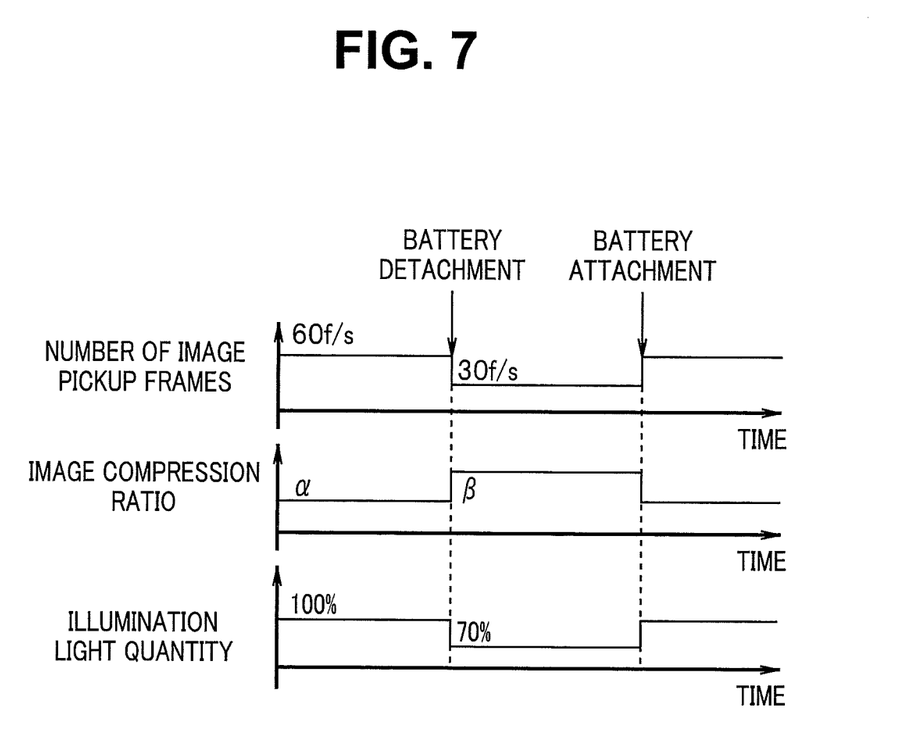
FIG. 7 is a timing chart for describing the operation of the embodiment.

FIG. 5 and FIG. 6 are flowcharts for describing the operation of the embodiment, and FIG. 7 is a timing chart for describing the operation of the embodiment. FIG. 5 illustrates an operation flow of the control portion 41, and the FIG. 6 illustrates an operation flow of the image processing and control portion 47.

The control portion 41 fetches the detection result of the detection portion 42 in step S1 in FIG. 5, and determines whether or not the battery 31 is in the state of being detachable from the connection portion (step S2). Now, it is assumed that the battery 31 is mounted on the operation portion 21. In this case, the control portion 41 turns on the switches a and b of the switch portion 43 and turns off the switch c of the switch portion 43 based on the detection result of the detection portion 42. Thus, battery drive is performed (step S3), and the power from the battery 31 is supplied to the power source portion 46 through the switch portion 43 and the power source line 46a. The power source portion 46 generates the power to be supplied to the respective portions of the wireless endoscope 1 based on the supplied power.

The control portion 41 sets the normal time operation mode to the image processing and control portion 47 in step S4. The image processing and control portion 47 determines whether or not the replacement time operation mode is set in step S11 in FIG. 6. When the normal time operation mode is set, the image processing and control portion 47 shifts the processing to step S12, and sets the photographing frame rate of the image pickup portion 50, the illumination light quantity of the illumination portion 49 and the compression ratio in the image processing. In FIG. 7, it is indicated that the photographing frame rate is set to 60 f/s, the compression ratio of the image is set to a, and the illumination light quantity is set to 100% in a period before battery detachment, that is, in the normal time operation mode. In this way, the respective portions of the wireless endoscope 1 are driven with normal power consumption.

Note that, in the normal time operation mode, the charging circuit 44 charges the capacitor 24 by the power from the power source line 46a. Thus, when the battery 31 is mounted, the capacitor 24 holds the power needed for operating the wireless endoscope 1.

Here, it is assumed that the battery is to be replaced due to a reason such as capacity shortage of the battery 31. An operator operates the detection portion 42 such as the mechanical switch in order to detach the battery 31. Thus, the control portion 41 determines that the battery is detachable in step S2.

In this case, the control portion 41 turns off the switches a and b of the switch portion 43 and turns on the switch c of the switch portion 43 based on the detection result of the detection portion 42. Thus, capacitor drive is performed (step S5), the power from the capacitor 24 is supplied to the discharging circuit 45, and the power is supplied from the discharging circuit 45 to the power source line 46a through the switch c. In this way, the power source portion 46 receives the power needed for the operation of the wireless endoscope 1, and generates the power for driving the respective portions.

The control portion 41 sets the replacement time operation mode to the image processing and control portion 47 in step S6 (step S6). The image processing and control portion 47 determines that the replacement time operation mode is set in step S11 in FIG. 6, shifts the processing to step S14, and resets the photographing frame rate of the image pickup portion 50, the illumination light quantity of the illumination portion 49 and the compression ratio in the image processing. In FIG. 7, it is indicated that the photographing frame rate is set to 30 f/s, the compression ratio of the image is set to β(>α), and the illumination light quantity is set to 70% in a period after the battery detachment, that is, in the replacement time operation mode.

The power consumption in the image pickup portion 50 can be reduced when the photographing frame rate is low. In addition, the power during transmission in the wireless portion 48 can be reduced when the compression ratio is high. Furthermore, the power consumption in the illumination portion 49 can be reduced when the illumination light quantity is low. In this way, in the replacement time operation mode, low power consumption drive with the power consumption lower than the power consumption in the normal time operation mode is performed (step S15).

Capacity of the capacitor 24 is set to a capacity capable of driving the wireless endoscope 1 for at least several minutes when it is the drive with the low power consumption, and by remounting the charged battery 31 within several minutes after the battery 31 is detached, the battery can be replaced without stopping the endoscopic observation by the wireless endoscope 1.

When the battery 31 is mounted again, the control portion 41 controls the switch portion 43 based on the detection result of the detection portion 42 and performs the battery drive (step S3). The power source portion 46 generates the power to be supplied to the respective portions of the wireless endoscope 1 based on the power supplied from the battery 31 through the power source line 46a.

In addition, the control portion 41 sets the normal time operation mode to the image processing and control portion 47 in step S4, and the image processing and control portion 47 shifts the processing to step S12, and resets the photographing frame rate of the image pickup portion 50, the illumination light quantity of the illumination portion 49 and the compression ratio in the image processing. In this way, as illustrated in FIG. 7, in the period after the battery attachment, the photographing frame rate is returned to 60 f/s, the compression ratio of the image is returned to α, and the illumination light quantity is returned to 100%. In this way, the respective portions of the wireless endoscope 1 are returned to the drive with the normal power consumption.

In this way, in the present embodiment, even in a case of replacing the battery, the operation of the endoscope can be continued by utilizing the power from the capacitor. Thus, photographing of the object can be continued without canceling a best angle before, after and in a middle of battery replacement, it is not needed to perform a complicated operation for obtaining the best angle, resupply of power source, various kinds of setting operations or the like accompanying the battery replacement, and a procedure can be smoothly advanced. In addition, in the replacement time operation mode, the operation with the power consumption lower than the power consumption in the normal time operation mode is possible, and even in the case of using the capacitor of relatively small capacity, the wireless endoscope can be driven for a sufficient time period needed for the replacement of the battery. Therefore, as the capacitor, the one of relatively light weight can be adopted, and operability is not deteriorated.

In addition, the present invention is not limited to each embodiment described above as it is, and components can be modified and embodied without departing from the scope in an implementation phase. In addition, by appropriate combinations of the plurality of components disclosed in each embodiment described above, various inventions can be formed. For example, some components in the entire components indicated in the embodiment may be deleted. Further, the components over the different embodiments may be appropriately combined.

What is claimed is:

1. A wireless endoscope comprising:
    an endoscope body including:
        a camera configured to pick up an image of an object, and
        a power storage component including a capacitor or a secondary battery, the capacitor or the secondary battery being configured to store power;
    a first battery configured to attachably and detachably connect to the endoscope body, the first battery being configured to generate power used for endoscopic observation by the wireless endoscope;
    a detection portion configured to detect a connection state or a disconnection state of the first battery to the endoscope body, the connection state or disconnection state of the first battery being detected based on: (i) a state of a mechanical switch including a lock mechanism for fixing the first battery to the endoscope body, or (ii) an electrical connection state between a terminal of the first battery and the endoscope body;
    a charging circuit configured to charge the capacitor or the secondary battery in the power storage component; and
    a processor configured to:
        conduct a first charging path from the first battery to the charging circuit to provide the power to charge the power storage component and render non-conductive a second charging path from the power storage component to the endoscope body, during a normal time operation mode of performing the endoscopic observation with the power from the first battery,
        in response to the detection portion detecting the disconnection state of the first battery, conduct the second charging path to provide the power from the power storage component to the endoscope body,
        set a replacement time operation mode to provide the power from the power storage component for the endoscopic observation and performing the endoscopic observation at a lower power compared to a normal time operation mode of performing the endoscopic observation with the power from the first battery, and
        restore the normal time operation mode from the replacement time operation mode in response to the detection portion detecting the connection state to the endoscope body by the first battery.

2. The wireless endoscope according to claim 1, further comprising:
    a light source provided in the endoscope body, the light source being configured to illuminate the object, wherein:
    the processor is configured to:
        perform image processing on an image from the camera;
        wirelessly transmit the image after the image processing to an outside environment of the wireless endoscope; and
        perform power consumption reduction that is at least one of: (A) reduction of an illumination light quantity by the light source, (B) reduction of a photographing frame rate of the camera, and (C) an increase of a compression ratio of the image, compared to the normal time operation mode, during the replacement time operation mode.

3. The wireless endoscope according to claim 2, wherein the processor executes at least the reduction of the illumination light quantity by the light source during the replacement time operation mode.

4. The wireless endoscope according to claim 1, wherein the processor renders the second charging path non-conductive by disconnecting a switch connecting the power storage component and the endoscope battery.

5. The wireless endoscope according to claim 1, further comprising:
   a discharging circuit configured to supply power from the power storage component to the endoscope body.

* * * * *